(12) United States Patent
Young et al.

(10) Patent No.: US 8,696,731 B2
(45) Date of Patent: Apr. 15, 2014

(54) LOCK/FLOATING MARKER BAND ON PUSHER WIRE FOR SELF-EXPANDING STENTS OR MEDICAL DEVICES

(75) Inventors: Eugene Young, Union City, CA (US); Chung Hao Yeh, Aliso Viejo, CA (US); Christopher G. M. Ken, San Mateo, CA (US); Thu Anh Ho, San Jose, CA (US)

(73) Assignee: Depuy Synthes Products, LLC, Raynham, MA (US)

(*) Notice: Subject to any disclaimer, the term of this patent is extended or adjusted under 35 U.S.C. 154(b) by 224 days.

(21) Appl. No.: 13/158,223

(22) Filed: Jun. 10, 2011

(65) Prior Publication Data

US 2012/0316636 A1    Dec. 13, 2012

(51) Int. Cl.
    *A61F 2/06*      (2013.01)
    *A61B 17/00*      (2006.01)

(52) U.S. Cl.
     USPC ........... 623/1.11; 606/194; 606/195; 606/198

(58) Field of Classification Search
     USPC ................. 606/194, 195, 198; 623/1.11–1.16
     See application file for complete search history.

(56) References Cited

U.S. PATENT DOCUMENTS

| | | | |
|---|---|---|---|
| 3,485,234 A | 12/1969 | Stevens | |
| 4,586,923 A | 5/1986 | Gould et al. | |
| 4,665,918 A | 5/1987 | Garza et al. | |
| 5,368,592 A | 11/1994 | Stern et al. | |
| 5,391,146 A | 2/1995 | That et al. | |
| 5,571,086 A | 11/1996 | Kaplan et al. | |
| 5,755,708 A | 5/1998 | Segal | |
| 5,776,141 A | 7/1998 | Klein et al. | |
| 5,782,855 A | 7/1998 | Lau et al. | |
| 5,797,952 A | 8/1998 | Klein | |
| 5,989,280 A | 11/1999 | Euteneuer et al. | |
| 6,168,579 B1 | 1/2001 | Tsugita | |
| 6,171,328 B1 | 1/2001 | Addis | |
| 6,179,859 B1 | 1/2001 | Bates et al. | |
| 6,183,481 B1 | 2/2001 | Lee et al. | |
| 6,187,015 B1 | 2/2001 | Brenneman | |
| 6,245,045 B1 | 6/2001 | Stratienko | |
| 6,264,671 B1 | 7/2001 | Stack et al. | |
| 6,270,521 B1 | 8/2001 | Fischell et al. | |
| 6,280,465 B1 | 8/2001 | Cryer | |
| 6,296,622 B1 | 10/2001 | Kurz et al. | |
| 6,425,898 B1 * | 7/2002 | Wilson et al. | 606/108 |
| 6,607,551 B1 * | 8/2003 | Sullivan et al. | 623/1.11 |
| 6,679,909 B2 | 1/2004 | McIntosh et al. | |
| 6,989,024 B2 | 1/2006 | Hebert et al. | |
| 7,935,140 B2 * | 5/2011 | Griffin | 623/1.11 |
| 2001/0027323 A1 | 10/2001 | Sullivan, III et al. | |
| 2001/0037126 A1 | 11/2001 | Stack et al. | |

FOREIGN PATENT DOCUMENTS

| | | |
|---|---|---|
| EP | 1880695 A1 | 1/2008 |
| WO | 9639998 A2 | 12/1996 |
| WO | 9707756 A1 | 3/1997 |
| WO | 0071058 A1 | 11/2000 |
| WO | 0149214 A1 | 7/2001 |
| WO | 03041610 A2 | 5/2003 |

OTHER PUBLICATIONS

European Search Report, Oct. 23, 2012, 6 pages.

* cited by examiner

*Primary Examiner* — Tuan V Nguyen
(74) *Attorney, Agent, or Firm* — Fulwider Patton LLP

(57) ABSTRACT

An apparatus for deploying and retrieving a self-expanding intravascular stent includes an intravascular delivery wire and floating marker band movably retained over the intravascular stent delivery wire and releasably mounting the self-expanding intravascular stent. The floating marker band is movably retained to a fixed marker band, and a distance between the fixed marker band and the floating marker band is variable and self-adjusting. One or more struts of the self-expanding intravascular stent are releasably constrained between a catheter wall and one or more sides of the floating marker band.

28 Claims, 4 Drawing Sheets

LOCK/FLOATING MARKER BAND ON PUSHER WIRE FOR SELF-EXPANDING STENTS OR MEDICAL DEVICES

BACKGROUND OF THE INVENTION

The present application relates to systems for deploying and/or retrieving intravascular stents, and more particularly relates to an apparatus for deploying and/or retrieving a self-expanding intravascular stent or medical device, including an intravascular stent delivery wire or pusher wire having one or more floating marker bands movably retained or constrained over the intravascular stent delivery wire or pusher wire for delivery and retrieval of an intravascular stent releasably placed over the one or more floating marker bands.

Intravascular stents are generally tubular and are actively or passively expanded radially in the vasculature of a patient. Such stents can be mounted over an expandable member or balloon of a balloon angioplasty catheter, for deployment of the stents by expansion of the balloon at the treatment site of the vasculature, such as at a stenosis or an aneurysm. Self-expanding stents can expand from a compressed delivery position to a larger diameter without the assistance of an expandable member or balloon.

Intravascular stent delivery systems for placement of an intravascular self-expanding stent at a treatment site in the vasculature typically have included a catheter that can be threaded through the vasculature with the self-expanding stent axially placed over a distal portion of the catheter. To position an intravascular stent at the treatment site of the vasculature, such as at a stenosis or an aneurysm, a guiding catheter is typically introduced into the vascular system of a patient, and advanced within the vasculature until the distal tip of the guiding catheter is adjacent to the treatment site. A guidewire is typically then advanced through the guiding catheter to the desired location, and then a dilatation or delivery catheter having a stent positioned on the dilatation or delivery catheter is advanced into the patient's vasculature over the guidewire, until the stent is properly positioned, after which the stent can be deployed at the treatment site.

One common technique for maintaining a self-expanding stent in a low profile configuration involves placement of a sheath or a sleeve over some or all of the stent, typically either to retain the stent in a compressed configuration around the catheter, to prevent body fluids from reaching the stent, or to protect the vasculature from the stent. Usually such a sheath or sleeve is retracted or released from the stent to allow the stent to achieve an expanded configuration.

A guidewire loaded stent is also known in which a radially expandable stent carried on a guidewire is covered in part by a retractable restraining sheath at or near a distal end of the guidewire. When the stent is placed at a treatment site, the restraining sheath is retracted to expose the stent and thus allow the stent to expand.

It would be desirable to provide an intravascular stent delivery system, including an intravascular stent delivery wire or pusher wire having one or more floating marker bands movably retained or constrained over the intravascular stent delivery wire or pusher wire for delivery and retrieval of a self-expanding intravascular stent or medical device releasably placed over the one or more floating marker bands, in order to provide a reduced diameter profile to permit delivery of an intravascular stent to smaller diameter and more delicate vessels of the vasculature, such as the neurovasculature.

It would also be desirable to provide an intravascular stent delivery wire or pusher wire having one or more floating marker bands movably retained or constrained over the intravascular stent delivery wire or pusher wire to allow for an integration of a proximal or distal segment of a self-expanding intravascular stent or medical device with the intravascular stent delivery wire or pusher wire to be fit into a catheter or tubular sheath and advanced and retracted within the catheter, within the vasculature of a patient, and to allow for the self-expanding intravascular stent or medical device to be retrieved back into the catheter after partial stent deployment.

It would also be desirable to provide an intravascular stent delivery wire or pusher wire having one or more floating marker bands movably retained or constrained over the intravascular stent delivery wire or pusher wire with a self-adjusting, variable gap between the self-expanding intravascular stent or medical device and a fixed marker band fixedly mounted on the intravascular stent delivery wire or pusher wire, in order to facilitate ease of advancement or retraction of the assembly and to allow for improved articulation of the self-expanding intravascular stent or medical device with respect to the intravascular stent delivery wire or pusher wire in a narrow vascular curvature which would otherwise not allow for traversing of the curve with conventional systems.

It also would be desirable to provide an intravascular stent delivery system including an intravascular stent delivery wire or pusher wire having one or more floating marker bands movably retained or constrained over the intravascular stent delivery wire or pusher wire for delivery and retrieval of an intravascular stent releasably placed over the one or more floating marker bands, so that the intravascular stent delivery wire or pusher wire tip is free to rotate during system advancement, for ease of navigating tortuous vascular anatomy.

It also would be desirable to provide an intravascular stent delivery system including an intravascular stent delivery wire or pusher wire with one or more floating marker bands having an outside circumference with a multi-sided or polygon shape, such as a square shape or pentagonal shape, for example, to allow for struts, legs or radiopaque markers of the self-expanding intravascular stent or medical device to extend beyond the one or more floating marker bands so that the struts, legs or radiopaque markers of the self-expanding intravascular stent or medical device are constrained by the catheter or tube wall and by one or more sides of the one or more floating marker bands, to allow for the self-expanding intravascular stent or medical device to interface with the intravascular stent delivery wire or pusher wire, and to allow the self-expanding intravascular stent or medical device to maintain column strength not to buckle under compression loads, particularly so that the self-expanding intravascular stent or medical device can be retrieved under tensile loads.

It also would be desirable to provide an intravascular stent delivery system including an intravascular stent delivery wire or pusher wire with one or more floating marker bands that can be located under the body of the self-expanding intravascular stent or medical device to provide support for the self-expanding intravascular stent or medical device, and to prevent or minimize stent buckling of the self-expanding intravascular stent or medical device. The present invention meets these and other needs.

SUMMARY OF THE INVENTION

Briefly and in general terms, the present invention provides for an apparatus for deploying and/or retrieving a self-expanding intravascular stent or medical device, including an intravascular delivery wire and one or more floating marker bands movably retained or constrained over the intravascular stent delivery wire or pusher wire, and configured to releasably mount a self-expanding intravascular stent or medical device on the one or more floating marker bands. In a presently preferred aspect, the outside circumference of the lock/floating marker band(s) has a multi-sided or polygon shape, such as a square shape or pentagonal shape, for example. In another presently preferred aspect, the intravascular stent delivery wire or pusher wire tip is free to rotate during system advancement for ease of navigating tortuous vascular anatomy.

In another presently preferred aspect, the one or more floating marker bands can be movably retained or constrained to a fixed marker band such as by a coil spring, braid or wire, for example, which can be connected to a ring or laser indentation on the fixed marker band, for example. The fixed marker band is fixedly attached to the intravascular stent delivery wire or pusher wire. Alternatively, the one or more floating marker bands can be movably retained or constrained to the intravascular stent delivery wire or pusher wire, such as by a coil spring, braid or wire, for example, which can be connected to a ring or laser indentation on the intravascular stent delivery wire or pusher wire, for example.

In another presently preferred aspect, a distance between the fixed marker band and the one or more floating marker bands is variable, and the distance between the fixed marker band and the one or more floating marker bands is self-adjusting in length by increasing or decreasing during advancement or retraction in response to anatomic vascular tortuosity to maintain smooth articulation.

In another presently preferred aspect, a proximal segment of the self-expanding intravascular stent or medical device is mounted over the one or more floating marker bands. Alternatively, a distal segment of the self-expanding intravascular stent or medical device can be mounted over the one or more floating marker bands. Preferably the stent to intravascular stent delivery wire or pusher wire articulation in a tight vascular curvature is self-adjusting to provide a variable gap or length between the stent and the fixed marker band to facilitate ease of assembly advancement or retraction.

In another presently preferred aspect, the apparatus for deploying and/or retrieving a self-expanding intravascular stent or medical device also includes a catheter or tubular sheath, and one or more struts or legs of the self-expanding intravascular stent or medical device extend beyond the one or more floating marker bands, so that the struts, legs or radiopaque markers of the self-expanding intravascular stent or medical device are constrained between the catheter or tube wall and at least one side of the one or more floating marker bands, which allows for the self-expanding intravascular stent or medical device to interface with intravascular stent delivery wire or pusher wire and for the self-expanding intravascular stent or medical device to maintain column strength and not to buckle under compression loads. In another presently preferred aspect, the self-expanding intravascular stent or medical device can be retrieved under tensile loads as the one or more floating marker bands will engage the struts, legs or radiopaque markers of the self-expanding intravascular stent or medical device.

In another presently preferred aspect, the apparatus for deploying and retrieving a self-expanding intravascular medical device, includes an intravascular pusher wire having a distal portion and a proximal portion and at least one floating marker band movably constrained over the intravascular pusher wire. The at least one floating marker band is configured to releasably mount a self-expanding intravascular medical device thereon and at least one fixed marker band is fixedly attached to the intravascular pusher wire, with the at least one floating marker band movably retained to the at least one fixed marker band by at least one constraining member. A distance between the at least one fixed marker band and the at least one floating marker band may be self-adjusting. The apparatus may also include a self-expanding intravascular medical device having a proximal segment mounted to at least one floating marker band. The apparatus may also include a tubular sheath having a wall within which the self-expanding intravascular medical device is disposed, the self-expanding intravascular medical device having at least one strut extending over the at least one floating marker band and constrained by the wall of the tubular sheath and by at least one side of the at least one floating marker band. The at least one floating marker band may have an outside circumference of a polygonal shape selected from the group of polygonal shapes consisting of square and pentagonal shapes. The at least one constraining member may include at least one coil spring. The at least one constraining member may include at least one braid. The at least one constraining member may include at least one retainer wire. The at least one retainer wire may be connected to a ring on the at least one fixed marker band. The intravascular stent delivery wire may have an intermediate portion disposed between the distal portion and the proximal portion. The intravascular stent delivery wire may include a coiled wire portion and a core wire portion with the coiled wire portion being wrapped around the core wire portion. The core wire portion may extend uniformly from the proximal portion to the distal portion of the intravascular stent delivery wire. The coiled wire portion may vary between at least two of: the proximal portion, the intermediate portion, and the distal portion, in at least one of the following properties: distance between adjacent coils, diameter of coils, thickness of wire, and material composition of wire. The at least one floating marker band may separate at least one of the following: (i) the proximal portion and the intermediate portion of the intravascular stent delivery wire and (ii) the distal portion and the intermediate portion of the intravascular stent delivery wire. The at least one floating marker band may separate the proximal portion and the distal portion of the intravascular stent delivery wire. The apparatus of may also include at least one fixed marker band fixedly attached to the intravascular stent delivery wire, with the at least one floating marker band movably retained to the at least one fixed marker band. The at least one fixed marker band may separate at least one of the following: (i) the proximal portion and the intermediate portion of the intravascular stent delivery wire and (ii) the distal portion and the intermediate portion of the intravascular stent delivery wire. The at least one fixed marker band may separate the proximal portion and the distal portion of the intravascular stent delivery wire. The apparatus may include two or more of the fixed marker bands, and a self-expanding intravascular stent, with the stent deployable over at least two of the two or more fixed marker bands. The apparatus may include two or more of the floating marker bands, and a self-expanding intravascular stent, with the stent deployable over at least two of the two or more floating marker bands. The apparatus may also include a self-expanding intravascular stent, with the stent deployable over the at least one floating marker band and the at least one fixed marker band. The apparatus may include a floating marker band movably retained to the intravascular stent delivery wire by at least one constraining member. The constraining member may include a braid, a coil spring, or a retainer wire. The retainer wire may be connected to a ring or an indentation on the intravascular stent delivery wire. The intravascular stent delivery wire may have a tip that is free to rotate during advancement of the intravascular stent delivery wire into a vasculature, for ease of navigating tortuous vascular anatomy. The at least one retainer wire may be connected to a ring on the intravascular stent delivery wire. The at least one retainer wire may be connected to an indentation on the at least one fixed marker band. The at least one retainer wire may be connected to an indentation on the intravascular stent delivery wire.

Other features and advantages of the present invention will become more apparent from the following detailed description of the preferred embodiments in conjunction with the accompanying drawings, which illustrate, by way of example, the operation of the invention.

DETAILED DESCRIPTION OF THE PREFERRED EMBODIMENTS

Figure 1:
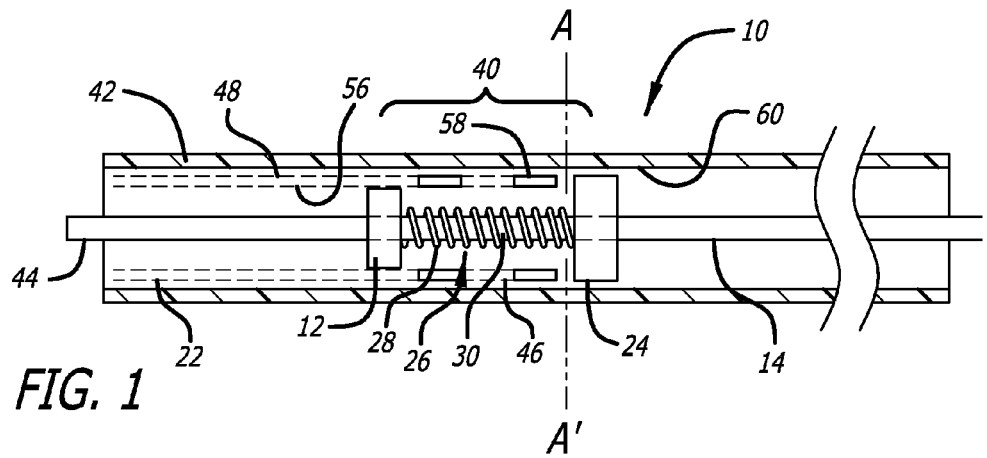
FIG. 1 is a cross-sectional schematic diagram of the apparatus for deploying and/or retrieving a self-expanding intravascular stent or medical device according to the invention.

Referring to the drawings, which are provided by way of example, and not by way of limitation, the present invention provides for an apparatus 10 for deploying and/or retrieving a self-expanding intravascular stent or medical device. The apparatus includes one or more floating marker bands 12 having a central aperture 13 therethrough and movably retained or constrained over an intravascular stent delivery wire or pusher wire 14 extending through the central aperture of the one or more floating marker bands.

The intravascular delivery wire or pusher wire includes a proximal portion 16, a distal portion 18, and an intermediate portion 20 in between the proximal and distal portions. In some embodiments, additional intermediate portions may be provided. The wire may be uniform throughout and across the respective portions or it may vary in one or more attributes from one portion to the next.

The one or more floating marker bands are configured to releasably mount a self-expanding intravascular stent or medical device 22 on the one or more floating marker bands. One or more fixed marker bands 24, typically having an outside circumference with a round shape, are fixedly anchored to the intravascular stent delivery wire or pusher wire.

In some embodiments, the intravascular delivery wire or pusher wire comprises a constraining member 26 such as a member having a coiled wire portion 28, and a core wire portion 30. The core wire portion may be straight or linear with the coiled wire portion wrapped around it, for example in a helical manner. The core wire portion may be uniform from one portion to the next with the coiled wire portion varying between two or more of the portions. For example, the coiled wire portion may vary with respect to one or more of the following attributes: distance between adjacent coils, diameter of coils, thickness of wire, and material composition of wire.

Figure 4:
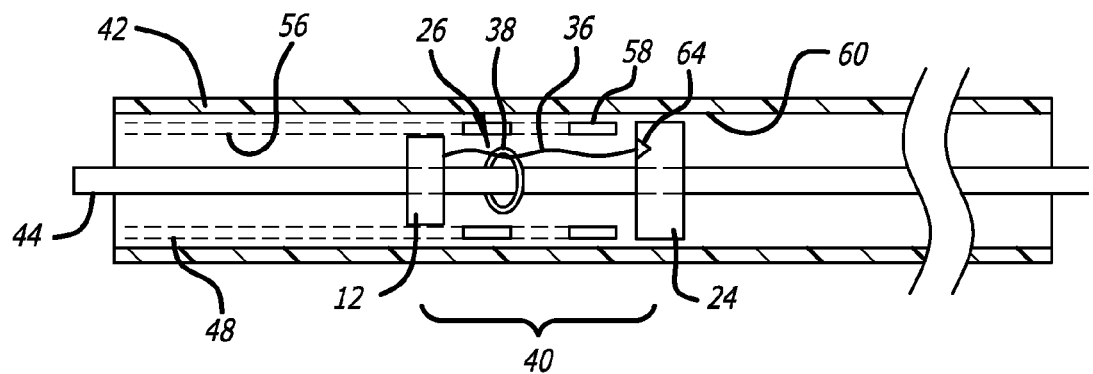
FIG. 4 is a cross-sectional schematic diagram of a third variation of the apparatus for deploying and/or retrieving a self-expanding intravascular stent or medical device according to the invention.
Figure 5:
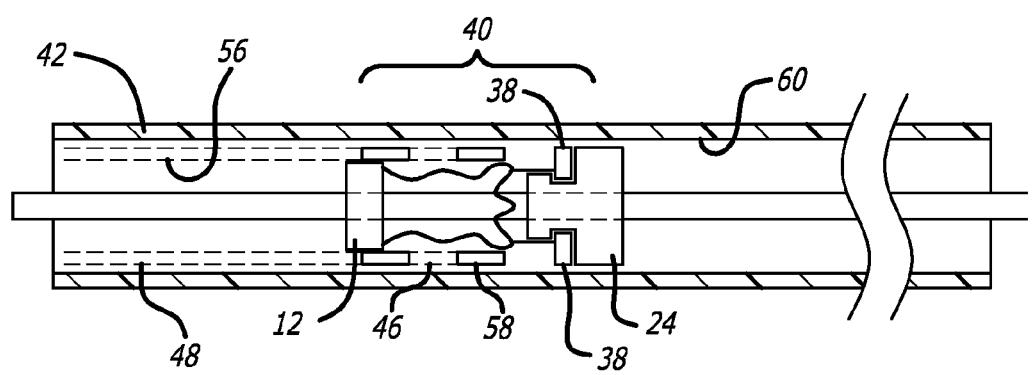
FIG. 5 is a cross-sectional schematic diagram of a fourth variation of the apparatus for deploying and/or retrieving a self-expanding intravascular stent or medical device according to the invention.

For example, as is illustrated in FIGS. 1-5, the one or more floating marker bands can be movably retained or constrained on the intravascular stent delivery wire or pusher wire by the constraining member, which can take the form of a coil spring 32, a braid 34, or a retainer wire 36, which can be connected to a ring 38, or a laser indentation 64 on the intravascular stent delivery wire or pusher wire or fixed marker band (see FIGS. 4 and 5).

The distance 40 between the fixed marker band and the one or more floating marker bands is dictated by the self-expanding intravascular stent or medical device design. The distance between the one or more floating marker bands and the fixed band is variable, or not constant, and will self-adjust in length by increasing or decreasing during advancement or retraction in response to anatomic vascular tortuosity to maintain smooth articulation. The stent to intravascular stent delivery wire or pusher wire articulation in a tight vascular curvature is self-adjusting to provide a variable gap or length between the self-expanding intravascular stent or medical device and the fixed marker band to facilitate ease of assembly advancement or retraction.

Figure 2:
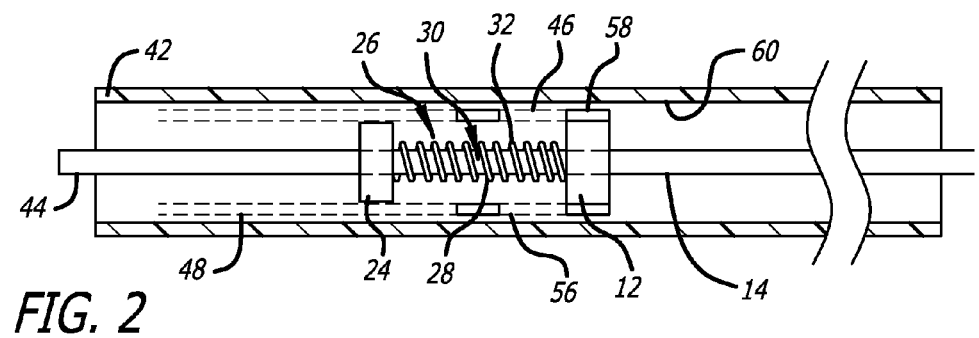
FIG. 2 is a cross-sectional schematic diagram of a first variation of the apparatus for deploying and/or retrieving a self-expanding intravascular stent or medical device according to the invention.
Figure 3:
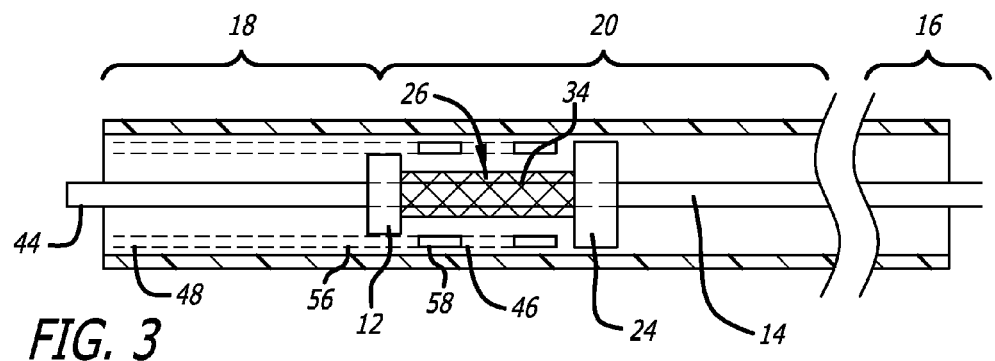
FIG. 3 is a cross-sectional schematic diagram of a second variation of the apparatus for deploying and/or retrieving a self-expanding intravascular stent or medical device according to the invention.
Figure 6:
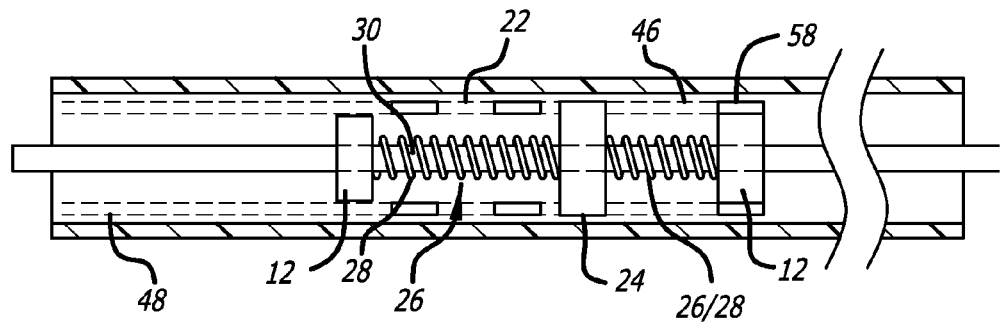
FIG. 6 is a cross-sectional schematic diagram of the apparatus for deploying and/or retrieving a self-expanding intravascular stent or medical device according to the invention as in FIG. 1, with an additional floating marker band added to the other side of the fixed marker band.
Figure 7:
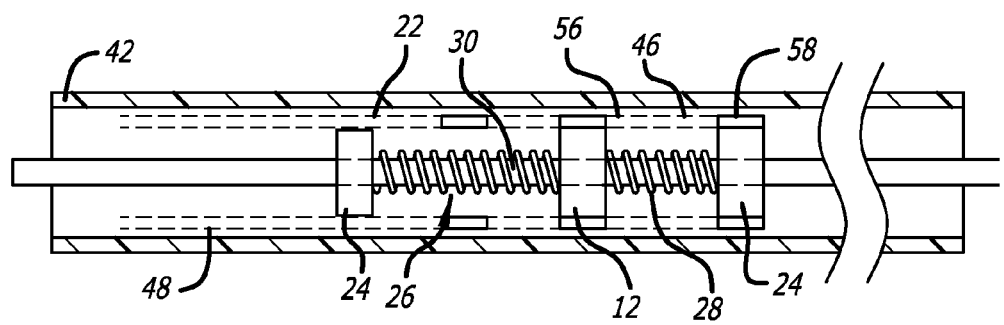
FIG. 7 is a cross-sectional schematic diagram of a first variation of the apparatus for deploying and/or retrieving a self-expanding intravascular stent or medical device according to the invention as in FIG. 2, with an additional fixed marker band added to the other side of the floating marker band.
Figure 8:
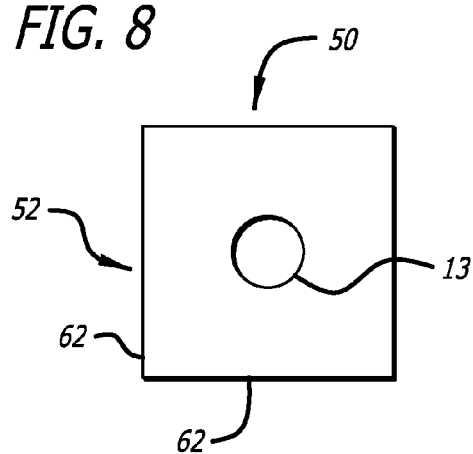
FIG. 8 is a plan view of a floating marker band having an outside circumference with a square shape.
Figure 9:
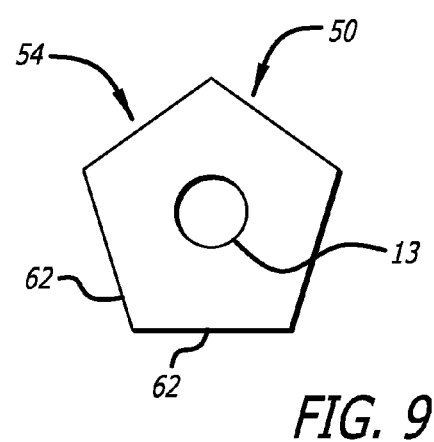
FIG. 9 is a plan view of a floating marker band having an outside circumference with a pentagonal shape.
Figure 10:
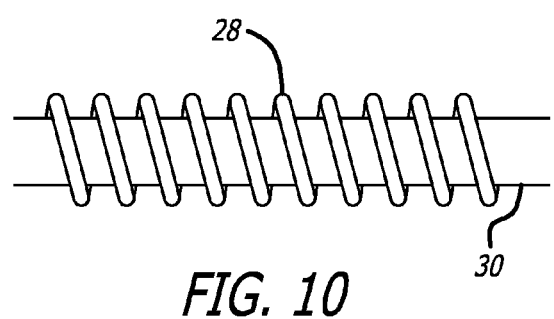
FIG. 10 is a cross-sectional schematic diagram of one embodiment of the intravascular delivery wire or pusher wire according to the present invention in which the wire includes an inner core wire portion and an outer coil wire portion.
Figure 11:
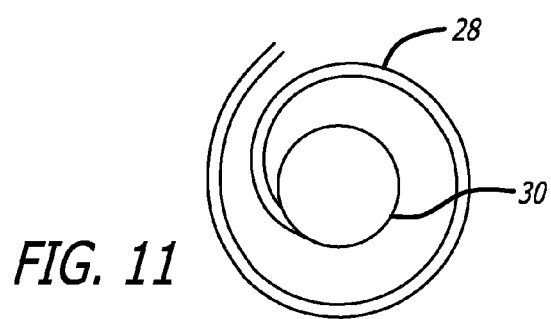
FIG. 11 is a plan view of one embodiment of the intravascular delivery wire or pusher wire according to the present invention in which the wire includes an inner core wire portion and an outer coil wire portion.

This assembly is intended to fit into a catheter or tubular sheath 42. The intravascular stent delivery wire or pusher wire tip 44 is free to rotate during system advancement for ease of navigating tortuous vascular anatomy. This invention is suitable for integration with a proximal segment 46 of the self-expanding intravascular stent or medical device or with a distal segment 48 of the self-expanding intravascular stent or medical device. Proximal integration is optimal for system advancement, deployment and stent retraction. As is illustrated in FIGS. 1 and 3-5, the one or more floating marker bands may be distal to the fixed marker band, or may be proximal to the fixed marker band as is shown in FIG. 2, or may be both distal and proximal to the fixed marker band as is shown in FIGS. 6-7. There may be one or more floating marker bands distal to the fixed marker band and one or more floating marker band proximal to the fixed marker band as shown in FIG. 6. Or, there may be one floating marker band 12 distal in relationship to a first fixed marker band 24 and proximal in relationship to a second fixed marker band 24 as shown in FIG. 7.

The outside circumference 50 of the one or more floating marker bands has a multi-sided or polygon shape, such as a square shape 52 or a pentagonal shape 54, for example. This allows for the struts or legs 56 or radiopaque markers 58 of a stent to extend beyond the one or more floating marker bands so that the struts, legs or radiopaque markers of the stent are constrained by the catheter or tube wall 60, and by at least one side 62 of the one or more floating marker bands. This allows for the stent to interface with intravascular stent delivery wire or pusher wire and for the stent end to maintain column strength and not to buckle under compression loads. The stent can be retrieved under tensile load as the one or more floating marker bands will engage proximal or distal struts or legs or radiopaque stent markers of the self-expanding intravascular stent or medical device. The one or more floating marker bands are preferably located under the stent body to provide stent support and to prevent or minimize stent buckling.

It should be readily apparent from the foregoing that the various portions (proximal, distal, intermediate) of the intravascular delivery wire or pusher wire may be separated from each other by one or more of a floating marker band and a fixed marker band. A stent or other medical device may be deployable between any two floating marker bands or fixed marker bands. A self-expanding intravascular stent or other medical device may be mounted on the marker bands. The arrangement of marker bands may include a single floating marker band and a single fixed marker band. In another embodiment, the arrangement may include a series of three or more marker bands. Still other variations of arrangements of one or more floating marker bands and one or more fixed marker bands together are possible for releasably mounting a stent or other medical device thereon and are considered within the spirit and scope of the present invention.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for deploying and retrieving a self-expanding intravascular stent, comprising:
    an intravascular stent delivery wire having a distal portion and a proximal portion;
    at least one floating marker band movably retained over said intravascular stent delivery wire and configured to releasably mount a self-expanding intravascular stent thereon; and
    at least one fixed marker band fixedly attached to the intravascular stent delivery wire, wherein said at least one floating marker band is movably retained to said at least one fixed marker band by at least one constraining member including at least one coil spring.

2. The apparatus of claim 1, wherein said at least one floating marker band separates the proximal portion and the distal portion of the intravascular stent delivery wire.

3. The apparatus of claim 1, comprising two or more of the floating marker bands, and further comprising a self-expanding intravascular stent, wherein the stent is deployable over at least two of the two or more floating marker bands.

4. The apparatus of claim 1, wherein the intravascular stent delivery wire comprises a freely rotatable tip configured to freely rotate during advancement of the intravascular stent delivery wire into a vasculature, for ease of navigating tortuous vascular anatomy.

5. The apparatus of claim 1, further comprising a self-expanding intravascular stent having a proximal segment mounted to said at least one floating marker band.

6. The apparatus of claim 5, further comprising a catheter having a wall within which the self-expanding intravascular stent is disposed, the self-expanding intravascular stent having at least one strut extending over said at least one floating marker band such that said at least one strut of the self-expanding intravascular stent is constrained by the catheter wall and by at least one side of said at least one floating marker band.

7. The apparatus of claim 1, wherein said at least one floating marker band has an outside circumference having a multi-sided shape.

8. The apparatus of claim 7, wherein the multi-sided shape is selected from the group of multi-sided shapes consisting of square and pentagonal shapes.

9. The apparatus of claim 1, wherein the intravascular stent delivery wire comprises an intermediate portion disposed between the distal portion and the proximal portion.

10. The apparatus of claim 9, wherein said at least one floating marker band separates at least one of the following: (i) the proximal portion and the intermediate portion of the intravascular stent delivery wire and (ii) the distal portion and the intermediate portion of the intravascular stent delivery wire.

11. The apparatus of claim 9, wherein the intravascular stent delivery wire comprises a coiled wire portion and a core wire portion, the coiled wire portion being wrapped around the core wire portion.

12. The apparatus of claim 11, wherein the core wire portion extends uniformly from the proximal portion to the distal portion of the intravascular stent delivery wire.

13. The apparatus of claim 12, wherein the coiled wire portion varies between at least two of: the proximal portion, the intermediate portion, and the distal portion, in at least one of the following properties: distance between adjacent coils, diameter of coils, thickness of wire, and material composition of wire.

14. The apparatus of claim 9, further comprising at least one fixed marker band fixedly attached to the intravascular stent delivery wire, wherein said at least one floating marker band is movably retained to said at least one fixed marker band.

15. The apparatus of claim 14, wherein said at least one fixed marker band separates at least one of the following: (i) the proximal portion and the intermediate portion of the intravascular stent delivery wire and (ii) the distal portion and the intermediate portion of the intravascular stent delivery wire.

16. The apparatus of claim 1, wherein a distance between said at least one fixed marker band and said at least one floating marker band is variable.

17. The apparatus of claim 1, wherein said at least one fixed marker band separates the proximal portion and the distal portion of the intravascular stent delivery wire.

18. The apparatus of claim 1, comprising two or more of the fixed marker bands, and further comprising a self-expanding intravascular stent, wherein the stent is deployable over at least two of the two or more fixed marker bands.

19. The apparatus of claim 1, further comprising a self-expanding intravascular stent, wherein the stent is deployable over said at least one floating marker band and said at least one fixed marker band.

20. The apparatus of claim 1, wherein said at least one constraining member comprises at least one braid.

21. The apparatus of claim 1, wherein said at least one floating marker band is movably retained to said intravascular stent delivery wire by at least one constraining member.

22. The apparatus of claim 21, wherein said at least one constraining member comprises an element selected from the group consisting of a braid and a coil spring.

23. An apparatus for deploying and retrieving a self-expanding intravascular medical device, comprising:
 an intravascular pusher wire having a distal portion and a proximal portion;
 at least one floating marker band movably constrained over the intravascular pusher wire, said at least one floating marker band being configured to releasably mount a self-expanding intravascular medical device thereon; and
 at least one fixed marker band fixedly attached to the intravascular pusher wire, wherein said at least one floating marker band is movably retained to said at least one fixed marker band by at least one constraining member including at least one coil spring.

24. The apparatus of claim 23, wherein a distance between said at least one fixed marker band and said at least one floating marker band is self-adjusting.

25. The apparatus of claim 23, wherein said at least one floating marker band has an outside circumference having a polygonal shape selected from the group of polygonal shapes consisting of square and pentagonal shapes.

26. The apparatus of claim 23, wherein said at least one constraining member comprises at least one braid.

27. The apparatus of claim 23, further comprising a self-expanding intravascular medical device having a proximal segment mounted to said at least one floating marker band.

28. The apparatus of claim 27, further comprising a tubular sheath having a wall within which the self-expanding intravascular medical device is disposed, the self-expanding intravascular medical device having at least one strut extending over said at least one floating marker band and constrained by the wall of the tubular sheath and by at least one side of said at least one floating marker band.

* * * * *